United States Patent
Galan

(10) Patent No.: US 6,306,387 B1
(45) Date of Patent: *Oct. 23, 2001

(54) ANTIGEN DELIVERY SYSTEM

(75) Inventor: Jorge E. Galan, Strongs Neck, NY (US)

(73) Assignee: The Research Foundation of State University of New York, Albany, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/987,691

(22) Filed: Dec. 9, 1997

Related U.S. Application Data
(60) Provisional application No. 60/047,955, filed on May 29, 1997.

(51) Int. Cl.[7] .......................... A01N 63/00; A01N 65/00; C07K 14/00; C12N 15/63

(52) U.S. Cl. .................. 424/93.2; 424/93.1; 424/9.1; 424/9.2; 435/320.1; 530/350; 530/402; 530/403; 530/825

(58) Field of Search .................. 424/93.1, 93.2, 424/9, 9.1; 514/44; 435/320.1, 252.3; 800/2; 530/350, 402, 403, 825

(56) References Cited

PUBLICATIONS

Valentine et al. Induction of SIV capsid–specific CTL and mucosal sIgA in mice immunized with a recombinant S. typhimurium aroA mutant. Vaccine 14:138–146, Feb. 1996.*

Ikonomidis et al. Delivery of viral antigen to the class I processing and presentation pathway by Listeria monocytogenes. J. Exp. Med. 180:2209–2218, Dec. 1994.*

Collazo, CM and Galan, JE The invasion–associated type III system of Salmonella typhimurium directs the translocation of Sip proteins into the host cell. Molec. Microbiol. 24:747–756, May 1997.*

Hess et al. Superior efficacy of secreted over somatic antigen display in recombinant Salmonella vaccine induced protection against listeriosis. Proc. Natl. Acad. Sci. USA 93:1458–1463, Feb. 1996.*

Cheng et al. Two independent type III secretion mechanisms for YopE in Yersinia enterocolitica. 24:757–765, May 1997.*

Karem et al. Protective immunity against herpes simplex virus (HSV) type 1 following oral administration of recombinant Salmonella typhimurium vaccine strains expressing HSV antigens. J. of Gen. Virol. 78:427–434, Feb. 1997.*

Gentschev et al. The Escherichia coli hemolysin secretion apparatus—versatile antigen delivery system in attenuated Salmonella. Behring Inst. Mitteilungen 98:103–113, see abstract only, 1997.*

Cornelis, GR The pYV plasmid, key element of Yersinia virulence. Medecine/Sciences 11:1295–1304, see summary only, 1995.*

Valentine, P.J. et al., Vaccine 14(2):138–146 (1996).

Karem, K.L. et al., Journal of General Virology 78:427–434 (1997).

Ikonomidis, G., et al., J Exp Med 180:2209–2218 (Dec. 1994).

Gentschev, I., et al., Behring Inst. Mitt 98:103–113 (1997).

Hess, J., et al., Proc Natl Acad Sci USA 93:1458–1463 (Feb. 1996).

Cornelis, G.R., Medicine/Sciences 11:1295–1304 (1995).

Cheng, L.W. et al., Molecular Microbiology 24(4):757–765 (1997).

Kubori, T., et al., Science 280:602–605 (Apr. 24, 1998).

Collazo, C.M., et al., Infection and Immunity 64(9):3524–3531 (Sep. 1996).

Collazo, C.M., et al., Molecular Microbiology 15(1):25–38 (1995).

Eichelberg, K., et al., Journal of Bacteriology 176(15):4501–4510 (Aug. 1994).

Galan, J.E., Molecular Microbiology 20(2):263–271 (1996).

Galan, J.E. et al., Annu Rev Cell Dev Biol 12:221–255 (1996).

Galan, J.E. et al., Journal of Bacteriology 174(13):4338–4349 (Jul. 1992).

Ginocchio, C.C., et al., Cell 76:717–724 (Feb. 25, 1994).

Kaniga, K., et al., Journal of Bacteriology 177(24):7078–7085 (Dec. 1995).

Kaniga, K., et al., Molecular Microbiology 13(4):555–568 (1994).

Kaniga, K., et al. Journal of Bacteriology 177(14):3965–3971 (Jul. 1995).

Kaniga, K., et al., Molecular Microbiology 21(3):633–641 (1996).

(List continued on next page.)

Primary Examiner—Jill D. Martin
Assistant Examiner—Anne-Marie Baker
(74) Attorney, Agent, or Firm—Braman & Rogalskyj, LLP

(57) ABSTRACT

Provided is a method of stimulating a class I-restricted immune response to a protein of interest or antigenic portion thereof in a host, as well as a protein delivery vehicle for use in the method. A nucleic acid molecule encoding the protein of interest or antigenic portion thereof is introduced into an avirulent Salmonella spp., such that the resulting Salmonella encodes a chimeric protein comprising the protein of interest or antigenic portion thereof and an injectable protein which is a target of a type III secretion system or an injectable portion thereof. This resulting Salmonella can be introduced into a host, in which the Salmonella will inject the chimeric protein into the cytosol of the cells of the host. The injection of the chimeric protein results in the stimulation of a class I-restricted immune response to the protein of interest or antigenic portion thereof in the host.

20 Claims, No Drawings

OTHER PUBLICATIONS

Wood, M.W., et al., Molecular Microbiology 22(2):327–338 (1996).

Selander, R.K., et al., In "*Escherichia coli* and Salmonella—Cellular and Molecular Biology", 2d Ed., F. Neidhardt et al., Eds., ASM Press, Washington D.C., pp. 2691–2707 (1996).

Collazo, C.M., et al., Molecular Microbiology 24(4):747–756 (1997).

GenBank Accession No. AF043239 (Feb. 8, 1998) and Accession No. AAC02071 (Feb. 6, 1998).

Russmann, H., et al., Science 281(5376):565–568 (Jul. 24, 1998).

Fu, Y., et al., Journal of Bacteriology 180(13):3393–3399 (Jul. 1998).

Hardt, W., et al., Proc Natl Acad Sci USA 95:2574–2579 (Mar. 1998).

Fu, Y., et al., Molecular Microbiology 27(2):359–368 (1998).

Hardt, W., et al., Proc Natl Acad Sci USA 94:9887–9892 (Sep. 1997).

Collazo, C.M., et al., Gene 192:51–59 (1997).

* cited by examiner

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 19 amino acids
      (B) TYPE: amino acid
      (C) STRANDEDNESS: Not Relevant
      (D) TOPOLOGY: linear (ii) MOLECULE TYPE: peptide (xi) SEQUENCE DESCRIPTION: SEQ ID NO:1:

```
Ile Ala Ser Asn Glu Asn Met Glu Thr Met Glu Ser Ser Thr Leu Glu
1               5                   10                  15

Leu Arg Ser
```

(2) INFORMATION FOR SEQ ID NO:2:

(i) SEQUENCE CHARACTERISTICS:
      (A) LENGTH: 563 amino acids
      (B) TYPE: amino acid
      (C) STRANDEDNESS: Not Relevant
      (D) TOPOLOGY: linear (ii) MOLECULE TYPE: protein (xi) SEQUENCE DESCRIPTION: SEQ ID NO:2:

```
Met Leu Lys Tyr Glu Glu Arg Lys Leu Asn Asn Leu Thr Leu Ser Ser
1               5                   10                  15

Phe Ser Lys Val Gly Val Ser Asn Asp Ala Arg Leu Tyr Ile Ala Lys
                20                  25                  30

Glu Asn Thr Asp Lys Ala Tyr Val Ala Pro Glu Lys Phe Ser Ser Lys
            35                  40                  45

Val Leu Thr Trp Leu Gly Lys Met Pro Leu Phe Lys Asn Thr Glu Val
    50                  55                  60

Val Gln Lys His Thr Glu Asn Ile Arg Val Gln Asp Gln Lys Ile Leu
65                  70                  75                  80

Gln Thr Phe Leu His Ala Leu Thr Glu Lys Tyr Gly Glu Thr Ala Val
                85                  90                  95

Asn Asp Ala Leu Leu Met Ser Arg Ile Asn Met Asn Lys Pro Leu Thr
            100                 105                 110

Gln Arg Leu Ala Val Gln Ile Thr Glu Cys Val Lys Ala Ala Asp Glu
            115                 120                 125

Gly Phe Ile Asn Leu Ile Lys Ser Lys Asp Asn Val Gly Val Arg Asn
```

-continued

```
            130                 135                 140
Ala Ala Leu Val Ile Lys Gly Gly Asp Thr Lys Val Ala Glu Lys Asn
145                 150                 155                 160
Asn Asp Val Gly Ala Glu Ser Lys Gln Pro Leu Leu Asp Ile Ala Leu
                165                 170                 175
Lys Gly Leu Lys Arg Thr Leu Pro Gln Leu Glu Gln Met Asp Gly Asn
                180                 185                 190
Ser Leu Arg Glu Asn Phe Gln Glu Met Ala Ser Gly Asn Gly Pro Leu
            195                 200                 205
Arg Ser Leu Met Thr Asn Leu Gln Asn Leu Asn Lys Ile Pro Glu Ala
        210                 215                 220
Lys Gln Leu Asn Asp Tyr Val Thr Thr Leu Thr Asn Ile Gln Val Gly
225                 230                 235                 240
Val Ala Arg Phe Ser Gln Trp Gly Thr Cys Gly Gly Glu Val Glu Arg
                245                 250                 255
Trp Val Asp Lys Ala Ser Thr His Glu Leu Thr Gln Ala Val Lys Lys
                260                 265                 270
Ile His Val Ile Ala Lys Glu Leu Lys Asn Val Thr Glu Ile Ala Ser
            275                 280                 285
Asn Glu Asn Met Glu Thr Met Glu Ser Ser Thr Leu Glu Leu Arg Ser
        290                 295                 300
Thr Glu Leu Glu Lys Ile Glu Ala Gly Ala Pro Met Pro Gln Thr Met
305                 310                 315                 320
Ser Gly Pro Thr Leu Gly Leu Ala Arg Phe Ala Val Ser Ser Ile Pro
                325                 330                 335
Ile Asn Gln Gln Thr Gln Val Lys Leu Ser Asp Gly Met Pro Val Pro
            340                 345                 350
Val Asn Thr Leu Thr Phe Asp Gly Lys Pro Val Ala Leu Ala Gly Ser
        355                 360                 365
Tyr Pro Lys Asn Thr Pro Asp Ala Leu Glu Ala His Met Lys Met Leu
    370                 375                 380
Leu Glu Lys Glu Cys Ser Cys Leu Val Val Leu Thr Ser Glu Asp Gln
385                 390                 395                 400
Met Gln Ala Lys Gln Leu Pro Pro Tyr Phe Arg Gly Ser Tyr Thr Phe
                405                 410                 415
Gly Glu Val His Thr Asn Ser Gln Lys Val Ser Ser Ala Ser Gln Gly
            420                 425                 430
Glu Ala Ile Asp Gln Tyr Asn Met Gln Leu Ser Cys Gly Glu Lys Arg
        435                 440                 445
Tyr Thr Ile Pro Val Leu His Val Lys Asn Trp Pro Asp His Gln Pro
    450                 455                 460
Leu Pro Ser Thr Asp Gln Leu Glu Tyr Leu Ala Asp Arg Val Lys Asn
465                 470                 475                 480
Ser Asn Gln Asn Gly Ala Pro Gly Arg Ser Ser Asp Lys His Leu
                485                 490                 495
Pro Met Ile His Cys Leu Gly Gly Val Gly Arg Thr Gly Thr Met Ala
            500                 505                 510
Ala Ala Leu Val Leu Lys Asp Asn Pro His Ser Asn Leu Glu Gln Val
        515                 520                 525
Arg Ala Asp Phe Arg Asp Ser Arg Asn Asn Arg Met Leu Glu Asp Ala
    530                 535                 540
Ser Gln Phe Val Gln Leu Lys Ala Met Gln Ala Gln Leu Leu Met Thr
545                 550                 555                 560
```

Thr Ala Ser (2) INFORMATION FOR SEQ ID NO:3:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:3:

```
Arg Ser Glu Arg Pro Gln Ala Ser Gly Val Tyr Met Gly Asn
1               5                   10
```

(2) INFORMATION FOR SEQ ID NO:4:

(i) SEQUENCE CHARACTERISTICS:
        (A) LENGTH: 528 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:4:

```
Met Leu Lys Tyr Glu Glu Arg Lys Leu Asn Asn Leu Thr Leu Ser Ser
1               5                   10                  15

Phe Ser Lys Val Gly Val Ser Asn Asp Ala Arg Leu Tyr Ile Ala Lys
            20                  25                  30

Glu Asn Thr Asp Lys Ala Tyr Val Ala Pro Glu Lys Phe Ser Ser Lys
        35                  40                  45

Val Leu Thr Trp Leu Gly Lys Met Pro Leu Phe Lys Asn Thr Glu Val
    50                  55                  60

Val Gln Lys His Thr Glu Asn Ile Arg Val Gln Asp Gln Lys Ile Leu
65                  70                  75                  80

Gln Thr Phe Leu His Ala Leu Thr Glu Lys Tyr Gly Glu Thr Ala Val
                85                  90                  95

Asn Asp Ala Leu Leu Met Ser Arg Ile Asn Met Asn Lys Pro Leu Thr
            100                 105                 110

Gln Arg Leu Ala Val Gln Ile Thr Glu Cys Val Lys Ala Ala Asp Glu
        115                 120                 125

Gly Phe Ile Asn Leu Ile Lys Ser Lys Asp Asn Val Gly Val Arg Asn
    130                 135                 140

Ala Ala Leu Val Ile Lys Gly Gly Asp Thr Lys Val Ala Glu Lys Asn
145                 150                 155                 160

Asn Asp Val Gly Ala Glu Ser Lys Gln Pro Leu Leu Asp Ile Ala Leu
                165                 170                 175

Lys Gly Leu Lys Arg Thr Leu Pro Gln Leu Glu Gln Met Asp Gly Asn
            180                 185                 190

Ser Leu Arg Glu Asn Phe Gln Glu Met Ala Ser Gly Asn Gly Pro Leu
        195                 200                 205

Arg Ser Leu Met Thr Asn Leu Gln Asn Leu Asn Lys Ile Pro Glu Ala
    210                 215                 220

Lys Gln Leu Asn Asp Tyr Val Thr Thr Leu Thr Asn Ile Gln Val Gly
225                 230                 235                 240

Val Ala Arg Phe Ser Gln Trp Gly Thr Cys Gly Gly Glu Val Glu Arg
                245                 250                 255
```

```
Trp Val Asp Lys Ala Ser Thr His Glu Leu Thr Gln Ala Val Lys Lys
            260                 265                 270

Ile His Val Ile Ala Lys Glu Leu Lys Asn Val Thr Glu Arg Ser Glu
            275                 280                 285

Arg Pro Gln Ala Ser Gly Val Tyr Met Gly Asn Thr Glu Leu Glu Lys
            290                 295                 300

Ile Glu Ala Gly Ala Pro Met Pro Gln Thr Met Ser Gly Pro Thr Leu
305                 310                 315                 320

Gly Leu Ala Arg Phe Ala Val Ser Ser Ile Pro Ile Asn Gln Gln Thr
                325                 330                 335

Gln Val Lys Leu Ser Asp Gly Met Pro Val Pro Val Asn Thr Leu Thr
            340                 345                 350

Phe Asp Gly Lys Pro Val Ala Leu Ala Gly Ser Tyr Pro Lys Asn Thr
            355                 360                 365

Pro Asp Ala Leu Glu Ala His Met Lys Met Leu Leu Glu Lys Glu Cys
            370                 375                 380

Ser Cys Leu Val Val Leu Thr Ser Glu Asp Gln Met Gln Ala Lys Gln
385                 390                 395                 400

Leu Pro Pro Tyr Phe Arg Gly Ser Tyr Thr Phe Gly Glu Val His Thr
                405                 410                 415

Asn Ser Gln Lys Val Ser Ser Ala Ser Gln Gly Glu Ala Ile Asp Gln
                420                 425                 430

Tyr Ile Cys Asn Cys Leu Arg Gly Lys Ala Tyr Thr Ser Val Leu His
                435                 440                 445

Val Lys Asn Trp Pro Asp His Gln Pro Leu Pro Ser Thr Asp Gln Leu
            450                 455                 460

Glu Tyr Leu Ala Asp Arg Val Lys Asn Ser Asn Gln Asn Gly Ala Pro
465                 470                 475                 480

Gly Ala Ser Ser Ser Asp Lys His Leu Pro Met Ile His Cys Leu Ala
                485                 490                 495

Gly Val Gly Arg Thr Gly Thr Met Ala Gly Gly Leu Val Leu Lys Asp
            500                 505                 510

Asn Leu Ile Val Ile Trp Ser Arg Tyr Val Gln Ile Arg Ile Thr Thr
            515                 520                 525

(2) INFORMATION FOR SEQ ID NO:5:

(i) SEQUENCE CHARACTERISTICS:
        (A) LENGTH: 336 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:5:

Met Leu Lys Tyr Glu Glu Arg Lys Leu Asn Asn Leu Thr Leu Ser Ser
1               5                   10                  15

Phe Ser Lys Val Gly Val Ser Asn Asp Ala Arg Leu Tyr Ile Ala Lys
            20                  25                  30

Glu Asn Thr Asp Lys Ala Tyr Val Ala Pro Glu Lys Phe Ser Ser Lys
            35                  40                  45

Val Leu Thr Trp Leu Gly Lys Met Pro Leu Phe Lys Asn Thr Glu Val
            50                  55                  60

Val Gln Lys His Thr Glu Asn Ile Arg Val Gln Asp Gln Lys Ile Leu
65                  70                  75                  80
```

-continued

```
Gln Thr Phe Leu His Ala Leu Thr Glu Lys Tyr Gly Glu Thr Ala Val
                 85                  90                  95
Asn Asp Ala Leu Leu Met Ser Arg Ile Asn Met Asn Lys Pro Leu Thr
                100                 105                 110
Gln Arg Leu Ala Val Gln Ile Thr Glu Cys Val Lys Ala Ala Asp Glu
            115                 120                 125
Gly Phe Ile Asn Leu Ile Lys Ser Lys Asp Asn Val Gly Val Arg Asn
        130                 135                 140
Ala Ala Leu Val Ile Lys Gly Gly Asp Thr Lys Val Ala Glu Lys Asn
145                 150                 155                 160
Asn Asp Val Gly Ala Glu Ser Lys Gln Pro Leu Leu Ser Ala Ala Phe
                165                 170                 175
Glu Asp Leu Arg Val Ser Ser Phe Ile Arg Gly Thr Lys Val Val Pro
                180                 185                 190
Arg Gly Lys Leu Ser Thr Arg Gly Val Gln Ile Ala Ser Asn Glu Asn
            195                 200                 205
Met Glu Thr Met Glu Ser Ser Thr Leu Glu Leu Arg Ser Arg Tyr Trp
        210                 215                 220
Ala Ile Arg Thr Arg Ser Gly Gly Asn Thr Asn Gln Gln Arg Ala Ser
225                 230                 235                 240
Ser Gly Gln Ile Ser Ile Gln Pro Thr Phe Ser Val Gln Arg Asn Leu
                245                 250                 255
Pro Phe Asp Arg Pro Thr Ile Met Ala Ala Phe Thr Gly Asn Thr Glu
                260                 265                 270
Gly Arg Thr Ser Asp Met Arg Thr Glu Ile Ile Arg Leu Met Glu Ser
            275                 280                 285
Ala Arg Pro Glu Asp Val Ser Phe Gln Gly Arg Gly Val Phe Glu Leu
        290                 295                 300
Ser Asp Glu Lys Ala Ala Ser Pro Ile Val Pro Ser Phe Asp Met Ser
305                 310                 315                 320
Asn Glu Gly Ser Tyr Phe Phe Gly Asp Asn Ala Glu Glu Tyr Asp Asn
                325                 330                 335
```

ANTIGEN DELIVERY SYSTEM

This application claims priority of U.S. Provisional Patent Application No. 60/047,955, filed May 29, 1997.

The subject invention was made with support under Public Health Service Grant Nos. AI30492 and GM52543 of the National Institutes of Health.

FIELD OF THE INVENTION

The subject invention is directed generally to immune responses, and more particularly to a method of stimulating a class I-restricted immune response in a host and to a protein delivery system for use in such a method.

BACKGROUND OF THE INVENTION

Throughout this application various publications are referenced, many in parenthesis. Full citations for each of these publications are provided at the end of the Detailed Description. The disclosures of each of these publications in their entireties are hereby incorporated by reference in this application.

Most infectious disease agents gain entrance to the host through a mucosal surface, therefore the first line of defense is the mucosal immune system. In fact, protection against many microorganisms better correlates with local than systemic immune responses (Galan et al. 1986; Galan and Timaney 1985). The use of non-replicating antigens to stimulate mucosal immune responses has been hampered by the lack of adjuvants that effectively induce secretory immunity. Live, replicating antigens are known to better stimulate mucosal immunity partly because they tend to persist longer (Ganguly and Waldman 1980). Avirulent strains of *Salmonella typhimurium* endowed with the ability to express cloned genes from other pathogens have been used to stimulate a generalized mucosal immune response against the recombinant virulence antigens (Doggett and Curtiss 1992; Curtiss et al. 1988; Curtiss et al. 1990; Galan et al. 1988). This approach is based on the fact that *S. typhimurium* invades and proliferates in the gut-associated lymphoid tissue (GALT) (Carter and Collins 1974) and that antigens delivered into the GALT lead to an immune response at other mucosal sites (Cebra et al. 1976).

After oral ingestion, *Salmonella typhimurium* penetrates the cells of the intestinal epithelium (Takeuchi 1967). Once internalized, Salmonella are translocated through the epithelial cells to the lamina propria where they are later taken up by macrophages. During the translocation process, Salmonella transit inside endocytic vesicles where they undergo limited replication. This is unlike other invasive pathogens, such as Shigella spp. or *Listeria monocytogenes*, which escape the endocytic vesicles shortly after internalization and actively replicate in the cell cytosol.

The compartment in the eukaryotic cell in which a bacterium resides is very important when it is being considered as an antigen delivery vehicle, because its location will largely determine whether the antigen will be recognized in association with MHC class I or class II molecules. Antigens presented in the context of class I MHC molecules will predominantly induce cytotoxic T cells ($T_{ctl}$), while antigens recognized in association with MHC class II molecules will be more likely to stimulate T helper cells ($T_H$) (Harding et al. 1988; Chain et al. 1988; Allen 1987). This is of great importance in vaccine design since protection against different infectious agents requires different types of immune responses. Thus in general terms, $T_{ctl}$'s play a key role in protection against most viral and some intracellular bacterial pathogens while $T_H$'s are more important in responses against exogenous antigens that enter the processing cells (expressing class II molecules) by endocytosis (Long and Jacobson 1989; Long 1989; Kaufman 1988).

It has been established that processing of exogenous antigens involves endocytosis, partial degradation within the endocytic vacuole, and binding to class II MHC molecules. Processing of class I-restricted antigens also appears to involve proteolysis and recognition of antigen-derived peptides bound to MHC class I molecules, although this processing is not secondary to endocytosis. Rather, antigens synthesized within host cells (e.g., viral proteins), or antigens derived from intracellular bacteria that have the ability to exit the endocytic vacuole (e.g., *Listeria monocytogenes* and Shigella spp.), are processed and then preferentially associate with MHC class I molecules (Long and Jacobson 1989; Kaufman 1988).

Even though humoral (in particular mucosal) immune responses are an important part of the protective mechanisms against pathogens, it is clear that for efficient protection, cell-mediated immunity is often essential. This is particularly so when the pathogen in question is a virus or an intracellular bacterium. In many of these cases, class I restricted-immune responses are thought to be crucial for protection. This type of immune response is stimulated by proteins that are newly synthesized (e.g., viral antigens) or that otherwise gain access to the cytosol of the infected cell (e.g., Listeria antigens). *S. typhimurium* has the ability to invade (enter) mammalian cells. Unlike other facultative intracellular pathogens such as Listeria or Shigella spp., which gain access to the cytosol shortly after entry, Salmonella spp. remain inside the endocytic vesicle throughout their entire intracellular life cycle. Although there are some exceptions to this generalization (Aggarwal et al. 1990; Flynn et al. 1990), it appears that Salmonella is not very efficient at stimulating class I-restricted immune responses, which are known to be crucial for protection against viruses and a variety of intracellular pathogens (Gao et al. 1992; Yang et al. 1990). This has been clearly demonstrated using avirulent Salmonella strains expressing different antigens from influenza virus. In a series of very elegant studies (Brett et al. 1993; Tite et al. 1990a; Tite et al. 1990b), it was shown that mice vaccinated with avirulent strains of Salmonella expressing the influenza virus NP failed to mount a significant class I-restricted T cell response against the NP, although they successfully induced class II-restricted responses. On the contrary, class I-restricted responses against the NP were readily demonstrated in mice infected with the virus. As a consequence of this failure, recombinant Salmonella vaccine strains failed to protect mice against influenza virus challenge since in this model of NP immunization, protection is largely dependent on nucleoprotein-specific class I-restricted CD8$^+$ cells.

An essential feature of the pathogenesis of Salmonella spp. is their ability to stimulate a variety of host-cell responses (reviewed in Galan and Bliska 1996). These responses are largely dependent on the type of cell engaged by the bacteria. For example, in non-phagocytic cells such as those of the intestinal epithelium, Salmonella spp. induce profound cytoskeletal rearrangements, membrane ruffling and macropinocytosis which ultimately result in bacteria internalization. In macrophages, on the other hand, Salmonella spp. induce programmed cell death (Chen et al. 1996). Essential for the stimulation of these responses is the function of a specialized protein secretion system encoded at centisome 63 of the bacterial chromosome (reviewed in Galan 1996). This protein secretion system, termed type III, directs the export of a number of proteins, some of them with presumed effector function. Characteristic features of this protein secretion system, which has also been identified in several other animal and plant pathogenic bacteria, include: 1) the absence in the secreted proteins of a typical, cleavable, sec-dependent, signal sequence; 2) the requirement of several accessory proteins for the export process; 3) the export of the target proteins through both the inner and outer membranes; and 4) the requirement of activating extracellular signals for its full function (reviewed in Galan 1996). Studies of pathogenic Yersinia spp. have established that a similar type III secretion apparatus directs the translocation into the host cells of a number of putative effector proteins such as the bacterial outer proteins YopE, YOpH, YopM and YpkA (Rosqvist et al. 1994; Sory and Cornelis 1994; Persson et al. 1995; Sory et al. 1995; Hakansson et al. 1996). Such translocation is thought to occur in a polarized manner in which proteins are transferred directly from the bacteria to the host cells without secretion into the infection medium. A notion has therefore emerged that protein translocation into host cells is perhaps the main function of this type of protein secretion system. This hypothesis is further supported by the observation that type III protein secretion systems have always been identified as essential determinants involved in intimate interactions of bacterial pathogens with their hosts (reviewed in Galan and Bliska 1996).

Several Salmonella proteins that are exported through this pathway have been identified although it is not known which, if any, of these proteins is translocated into host cells.

A need exists for new methods for stimulating class I-restricted immune responses.

SUMMARY OF THE INVENTION

The subject invention addresses this need by providing a method for stimulating a class I-restricted immune response to a protein of interest or antigenic portion thereof in a host. The method comprises: introducing a nucleic acid molecule encoding a protein of interest or antigenic portion thereof into an avirulent Salmonella spp., the nucleic acid molecule being introduced so as to encode a chimeric protein comprising the protein of interest or antigenic portion thereof and an injectable protein which is a target of a type III secretion system or an injectable portion thereof; and introducing the resulting Salmonella spp. into a host, wherein the resulting Salmonella spp. injects the chimeric protein into the cytosol of cells of the host thereby stimulating a class I-restricted immune response to the protein of interest or antigenic portion thereof in the host.

The invention further provides a protein delivery vehicle which comprises: an avirulent Salmonella spp. encoding a chimeric protein, the chimeric protein comprising a protein of interest or an antigenic portion thereof and an injectable protein which is a target of a type III secretion system or an injectable portion thereof.

Further provided is a chimeric protein which comprises: a first amino acid sequence of an injectable protein which is a target of a type III secretion system or an injectable portion thereof; and a second amino acid sequence of a protein of interest or antigenic portion thereof introduced into the first amino acid sequence of the injectable protein or injectable portion thereof.

Also provided is a chimeric nucleic acid molecule which comprises: a first nucleic acid sequence encoding an injectable protein which is a target of a type III secretion system or an injectable portion thereof; and a second nucleic acid sequence encoding a protein of interest or antigenic portion thereof introduced into the first nucleic acid sequence of the injectable protein or injectable portion thereof, the second nucleic acid sequence being introduced so as to encode a chimeric protein comprising the protein of interest or antigenic portion thereof and the injectable protein or injectable portion thereof.

DETAILED DESCRIPTION OF THE INVENTION

As used herein, an "avirulent" Salmonella refers to a Salmonella which is not capable of causing disease in the host to which it is administered.

As further used herein, a "Salmonella encoding" refers to a Salmonella which has nucleic acid therein which encodes the referenced protein, either as extrachromosomal nucleic acid or as nucleic acid incorporated into the genome of the Salmonella.

The subject invention provides a method for stimulating a class I-restricted immune response to a protein of interest or antigenic portion thereof in a host. The method comprises: introducing a nucleic acid molecule encoding a protein of interest or antigenic portion thereof into an avirulent Salmonella spp., the nucleic acid molecule being introduced so as to encode a chimeric protein comprising the protein of interest or antigenic portion thereof and an injectable protein which is a target of a type III secretion system or an injectable portion thereof; and introducing the resulting Salmonella spp. into a host, wherein the resulting Salmonella spp. injects the chimeric protein into the cytosol of cells of the host thereby stimulating a class I-restricted immune response to the protein of interest or antigenic portion thereof in the host.

The invention further provides a protein delivery vehicle which comprises: an avirulent Salmonella spp. encoding a chimeric protein, the chimeric protein comprising a protein of interest or an antigenic portion thereof and an injectable protein which is a target of a type III secretion system or an injectable portion thereof. A host into which the protein delivery vehicle has been introduced is also provided. Suitable hosts include those in which a class I-restricted immune response is desirable, including, for example, humans.

Further provided is a chimeric protein which comprises: a first amino acid sequence of an injectable protein which is a target of a type III secretion system or an injectable portion thereof; and a second amino acid sequence of a protein of interest or antigenic portion thereof introduced into the first amino acid sequence of the injectable protein or injectable portion thereof.

Also provided is a chimeric nucleic acid molecule which comprises: a first nucleic acid sequence encoding an injectable protein which is a target of a type III secretion system or an injectable portion thereof; and a second nucleic acid sequence encoding a protein of interest or antigenic portion thereof introduced into the first nucleic acid sequence of the injectable protein or injectable portion thereof, the second nucleic acid sequence being introduced so as to encode a chimeric protein comprising the protein of interest or antigenic portion thereof and the injectable protein or injectable portion thereof.

In each of the above embodiments of the invention, the protein of interest is selected based on the desirability of stimulating a class I-restricted immune response thereto. The many pathogens known to exist and yet to be discovered are examples of sources of "proteins of interest". For example, microbial proteins may be of interest. These include, for example, proteins from bacterial, viral, parasitic, and protozoan pathogens. This list is not inclusive, and the concept of the subject invention is equally applicable to any "protein of interest" as defined above.

Furthermore, the particular injectable protein can be any protein which is a target of a type III secretion system (see Galan 1996; Rosqvist et al. 1994; Sory and Cornelis 1994; Persson et al. 1995; Sory et al. 1995; Hakansson et al. 1996; and Galan and Bliska 1996 for discussions of type III secretion systems suitable for use in the subject invention). Any type III secretion systems known to exist and yet to be discovered are examples of "type III secretion systems" in accordance with the subject invention. For example, currently known targets of bacterial type III secretion systems include the SptP, SipA, SipB, SipC, SipD, InvJ, SpaO, AvrA, and SopE proteins of Salmonella, the Yop and Ypk proteins of Yersinia (for example, YopE, YopH, YopM and YpkA), the Ipa proteins of Shigella, and the ExoS proteins of *Pseudomonas aeruginosa*.

Standard laboratory techniques known in the art of recombinant DNA and bacterial genetics can be used to construct chimeric proteins and to introduce a nucleic acid molecule encoding a protein of interest or antigenic portion thereof into an avirulent Salmonella spp. (see Sambrook et al. 1989). One commonly used method for introducing nucleic acid molecules into a cell is through the use of a plasmid vector. The use of viral vectors such as bacteriophage is another example of a known method for introducing nucleic acid molecules into a cell (the bacteriophage is used to introduce nucleic acid molecules into a bacterial cell).

The engineered Salmonella spp. can be introduced into a host (in which a class I-restricted immune response is desired to the protein of interest) by any methods known in the art, including for example, oral infection or injection.

Materials and Methods

Bacterial strains, cell lines and culture conditions

Bacterial strains used are listed on Table 1 and were grown under conditions that allow expression of components and targets of the invasion-associated type III system (Collazo and Galan 1996). Henle-407 cells were grown in Dulbecco's minimal essential medium (DMEM) containing 10% bovine calf serum.

Immunofluorescence staining

Henle-407 cells were grown to semi-confluency in 12 mm round glass coverslips that had been previously treated with poly-L-lysine. Cells were infected with different *S. typhimurium* strains in Hank's balanced salt solution (HBSS) for varying times as indicated in each experiment at a multiplicity of infection (m.o.i.) of ~25. When indicated, cytochalasin D was added to the cells 15 minutes before the infection at a concentration of 5 $\mu$g/ml. At this concentration, cytochalasin D effectively prevented bacterial internalization. In some experiments, gentamicin was added at a concentration of 100 $\mu$g/ml to eliminate extracellular bacteria. After infection, cells were washed three times with HBSS, fixed in 3.7% formaldehyde for 10 min, and permeabilized in 0.2% Triton X-100 in PBS for 2 minutes. After permeabilization, cells were washed three times with phosphate buffered saline containing 3% bovine serum albumin (PBS/BSA) and incubated for 30 min at room temperature with a 1:25 dilution in PBS/BSA of rabbit polyclonal antisera against SipB, SipC, AvrA, SptP and SopE. After washing three times with PBS/BSA, monolayers were incubated for 30 minutes at room temperature with fluorescein isothiocyanate (FITC)-labeled anti-rabbit IgG diluted 1:100 in PBS/BSA, washed three times with PBS and stained with DAPI (5 $\mu$g/ml). Coverslips were mounted on glass slides with Vectashield mounting medium (Vector Labs, Inc.) and visualized under a Nikon Diaphot 300 fluorescence microscope or under a confocal microscope (Odyssey, Noran Instruments, Middletown Wis.).

Detection of translocated bacterial proteins in S. typhimurium-infected Henle-407 cells Semi-confluent Henle-407 cells were grown in 100 mm tissue culture plates and infected with different strains of *S. typhimurium* at an m.o.i. of 50 in 2.5 ml HBSS for 90 min. Prior to the infection, bacterial cultures were centrifuged and resuspended in HBSS to eliminate culture supernatant proteins. After infection, non-adherent bacteria were removed and cells were washed three times with HBSS. The infection supernatant was combined with the material from the washes and centrifuged at 8,000 g for 20 min. The pellet containing non-adherent bacteria was resuspended in 200 $\mu$l PBS (non-adherent bacteria fraction). The supernatant was filtered through a 0.45 $\mu$m syringe filter (Gelman Sciences, Mich.) and proteins were precipitated by addition of 10% TCA and subsequent incubation at 4° C. for 1 hr (infection medium fraction). Infected cells were incubated for 30 minutes with DMEM containing 10% BCS and 100 $\mu$g/ml gentamicin to kill extracellular bacteria and subsequently washed thoroughly with HBSS. Cells were then treated with 30 $\mu$g/ml of proteinase K in HBSS for 15 min at 37° C. in a $CO_2$ incubator to eliminate cell-surface associated Sip proteins. After proteinase K treatment, 3 ml of chilled HBSS containing 2 mM PMSF were added. Cells detached during the proteinase treatment and were subsequently collected by low speed centrifugation (600 g for 10 minutes) and lysed in 1 ml of HBSS containing 0.1% Triton X-100 and 1 mM PMSF. The cell lysate was transferred to a microcentrifuge tube, treated with DNAse (10 $\mu$g/ml) and RNase (10 $\mu$g/ml) for 15 min at room temperature and centrifuged at 15,000 g for 10 minutes. The pellet was resuspended in PBS (Triton X-100 insoluble fraction) and the supernatant was filtered through a 0.45 $\mu$m syringe filter and proteins were precipitated in the presence of 10% TCA at 4° C. (Triton X-100 soluble fraction).

Western blot analysis

Samples were separated in a 10% discontinuous SDS-PAGE, and transferred to nitrocellulose membranes as described (Collazo and Galan 1996). SipB, SipC, AvrA, SptP and SopE proteins were detected by immunoblot analysis using monoclonal antibodies and enhanced chemiluminescence. For quantitation of the Sip proteins in the different cellular fractions, western blots were treated with monoclonal antibodies followed by alkaline phosphatase-labeled anti mouse antibody. Blots were developed by the addition of the fluorescence-emitting Attophos substrate (JBL, San Luis Obispo, Calif.) and scanned in a Molecular Dynamics Storm unit. The scanned membranes were quantified using the software ImageQuant version 1.1 (Molecular Dynamics) run on a Macintosh Power PC 8100 computer.

EXAMPLE I

SipB, SipC, SptP, AvrA and SopE are translocated into cultured Henle-407 cells in an independent manner This experiment was designed to investigate whether infection of cultured intestinal Henle-407 cells with wild-type *S. typhimurium* would result in the translocation of SipB, SipC, SptP, AvrA or SopE which are targets of the invasion-associated type III secretion system (Kaniga et al. 1995a; Kaniga et al. 1995b). Cultured intestinal Henle-407 cells were infected with the *S. typhimurium* wild-type strain SL1344 or its isogenic mutant strain SB136 which carries a non-polar mutation in invA, a gene that encodes an essential component of the invasion-associated type III secretion system (Galan et al. 1992). Two hours after infection, cells were fixed and processed for immunofluorescence staining with antibodies directed to SipB, SipC, AvrA, SptP and SopE as indicated in Materials and Methods.

A fluorescence signal was apparent in samples infected with wild-type *S. typhimurium* and stained with the anti SipB, SipC, AvrA, SptP and SopE antibodies. Henle-407 cells infected with the invA mutant strain SB136 exhibited no cell SipC staining. Optical sectioning and confocal microscopy determined that SipC, AvrA, SipB, SopE and SptP were equally distributed throughout the cytoplasm of cells infected with wild-type bacteria. To further demonstrate the translocation of AvrA, SipB, SipC, SptP and SopE into infected cells, cultured Henle-407 cells were infected with *Salmonella typhimurium*. Two hours after infection, a biochemical fractionation of the infected cells was carried out and the presence of these proteins in the different fractions was investigated by Western Blot analysis as indicated in the Materials and Methods. AvrA, SipB, SipC, SptP and SopE were present in the infection media and Triton X-100 soluble and insoluble fractions of Henle-407 infected cells.

These results indicate that SipB, SipC, SptP, SopE and AvrA are translocated into cultured Henle-407 cells and that such a translocation is dependent on the function of the type III protein secretion system encoded at centisome 63 on the *S. typhimurium* chromosome.

EXAMPLE II

Chimeric proteins between SptP, a target of the centisome 63 type III protein secretion system of Salmonella spp., and heterologous polypeptides are translocated into host cells.

Using recombinant DNA technology, a gene encoding a chimeric protein (termed SptP-NP) was constructed by introducing an oligonucleotide encoding a class I restricted epitope (SEQ ID NO:1: IASNENMETMESSTLELRS consisting of residues 365 through 384 of the influenza virus nucleoprotein) at residue 286 of the Salmonella SptP protein sequence. The sequence of the resulting chimeric protein (SptP-NP) is as follows (the influenza virus nucleoprotein epitope is depicted underlined and bold):

SEQ ID NO:2: MLKYEERKLNNLTLSSFSKVGVSN-DARLYIAKENTDKAYVAPEKFSSKVLTWLGK MPLFKNTEVVQKHTENIRVQDQKILQT-FLHALTEKYGETAVNDALLMSRINMNKP LTQR-LAVQITECVKAADEGFINLIKSKDN-VGVRNAALVIKGGDTKVAEKNNDVGA ESKQPLL-DIALKGLKRTLPQLEQMDGNSLRENFQE-MASGNGPLRSLMTNLQNLNK IPEAKQLNDYVT-TLTNIQVGVARFSQWGTCGGEVERWVDKASTHE LTQAVKKIHV IAKELKNVTEIASNENMET-MESSTLELRSTELEKIEAGAPMPQTMS-GPTLGLAR FAVSSIPINQQTQVKLSDG-MPVPVNTLTFDGKPVALAGSYPKNTPDALEAHM KML LEKECSCLVVLTSEDQMQAKQLPPYFRG-SYTFGEVHTNSQKVSSASQGEAIDQYN MQLSCGEKRYTIPVLHVKNWPDHQPLP-STDQLEYLADRVKNSNQNGAPGRSSSD KHLP-MIHCLGGVGRTGTMAAALVLKDNPHSN-LEQVRADFRDSRNNRMLEDASQF VQLKAMQAQLLMTTAS

A plasmid encoding SptP-NP was introduced into several strains of *Salmonella typhimurium* (listed in Table 1) and the resulting strains tested for their ability to direct the translocation of the chimeric protein into host cells. The translocation of the chimeric proteins was investigated by fluorescence microscopy and biochemical fractionation as described in Materials and Methods. Henle-407 cells were infected with strains of *S. typhimurium* encoding SptP-NP and after two hours of infection, cells were fixed and processed for immunofluorescence staining with a monoclonal antibody capable of detecting the chimeric protein. Infected cells showed intensive SptP-NP staining throughout the cell cytoplasm. Confocal microscopy established that the chimeric protein was distributed throughout the cell cytoplasm but was absent from the nucleus and plasma membranes of infected cells. These results indicate that *S. typhimurium* can translocate SptP-NP into host cells during infection.

Similar studies were carried out with two additional chimeric proteins. One chimeric protein (termed SptP-LCM) was constructed by introducing an epitope of the lymphocytic coriomeningitis (LCM) virus (SEQ ID NO:3: RSERPQASGVYMGN) at residue 286 of the Salmonella SptP protein sequence. The sequence of the resulting chimeric protein (SptP-LCM) is as follows (the LCM epitope is depicted underlined and bold):

SEQ ID NO:4: MLKYEERKLNNLTLSSFSKVGVSN-DARLYIAKENTDKAYVAPEKFSSKVLTWLGK MPLFKNTEVVQKHTENIRVQDQKILQT-FLHALTEKYGETAVNDALLMSRINMNKP LTQR-LAVQITECVKAADEGFINLIKSKDN-VGVRNAALVIKGGDTKVAEKNNDVGA ESKQPLL-DIALKGLKRTLPQLEQMDGNSLRENFQE-MASGNGPLRSLMTNLQNLNK IPEAKQLNDYVT-TLTNIQVGVARFSQWGTCGGEVERWVDKASTHE LTQAVKKIHV IAKELKNVTERSERPQAS-GVYMGNTELEKIEAGAPMPQTMS-GPTLGLARFAVSS IPINQQTQVKLSDG-MPVPVNTLTFDGKPVALAGSYPKNTPDALEAHM KMLLEKEC SCLVVLTSEDQMQAKQLPPYFRG-SYTFGEVHTNSQKVSSASQGEAIDQYICNCLRG KAYTSVLHVKNWPDHQPLPSTDQLEY-LADRVKNSNQNGAPGASSSDKHLPMIHC LAGVGRTGTMAGGLVLKDNLIVIWSRYVQIRITT

The other chimeric protein (SptP-NPc) was constructed by fusing the first 173 amino acids of SptP with residues 335 through 498 of the influenza virus nucleoprotein. The sequence of the resulting chimeric protein (SptP-NPc) was as follows (the influenza virus nucleoprotein portion is depicted underlined and bold):

SEQ ID NO:5: MLKYEERKLNNLTLSSFSKVGVSN-DARLYIAKENTDKAYVAPEKFSSKVLTWLGK MPLFKNTEVVQKHTENIRVQDQKILQT-FLHALTEKYGETAVNDALLMSRINMNKP LTQR-LAVQITECVKAADEGFINLIKSKDN-VGVRNAALVIKGGDTKVAEKNNDVGA ESKQPLLSAAFEDLRVSSFIRGTKV-VPRGKLSTRGVQIASNENMETMESST LELRSRY-WAIRTRSGGNTNQQRASSGQISIQPTFS-VQRNLPFDRPTIMAA FTGNTEGRTSDMRTEIIRLMESARPED-VSFQGRGVFELSDEKAASPIVPSF DMSNEGSY-FFGDNAEEYDN

When expressed in various strains of *S. typhimurium* both chimeric proteins (SptP-LCM and SptP-NPc) were translocated into host cells.

EXAMPLE III

Salmonella strains expressing chimeric proteins between SptP and influenza nucleoprotein peptide sequences can present a nucleoprotein epitope via the class I pathway in vitro.

To examine the ability of the different Salmonella strains (SL 1344 and $X^{3625}$) expressing SptP-Np and SptP-NPc to present the influenza virus nucleoprotein epitope via the class I presenting pathway in vitro, an assay was used based on the induction of IL-2 production in the T cell hybridoma 1192 upon presentation of the NP366–374 peptide in the context of class I $D^b$ molecules by the EL4 murine lymphoma cell line. EL4 cells (~$6\times10^7$), grown in Dulbecco's modified MEM with 10% fetal bovine serum, 10 mM HEPES, $5\times10^{-5}$ M 2-mercaptoethanol and without antibiotics (DMEM-10), were alternatively infected with $6\times10^9$ c.f.u. of the different strains of *S. typhimurium* (constructed as described in Example II) expressing either SptP-NP or SptP-NP. Infections were carried out as described (Kaniga et al. 1996). After infection, non-internalized or adhered bacteria were removed by washing, and cells further incubated in the presence of 100 µg/ml of gentamicin for 1 hour. A volume of 0.1 ml of DMEM-10 containing $2\times10^5$ EL4 cells infected with Salmonella were distributed into each well of 96-well plates in quadruplicate. To each well $1\times10^5$ 1192 T cell hybridoma effector cells (clones 12.164 or 7.9.3.28) in 0.1 ml of DMEM-10 were added. Plates were then incubated for 10 hours at 37° C., 100 µl of supernatant fluid removed from each well, divided in two aliquots, placed in individual wells of a 96 well plate and stored at –20° C. for subsequent IL-2 quantitation. The presence of IL-2 in the cell culture media aliquots was determined using the IL-2-dependent cell line CTLL-2 (ATCC TIB-214) as follows. To the thawed plates containing the test samples (EL4+1192 supernatants) $5\times10^4$ CTLL-2 cells in 100 µl of DMEM-10 were added and the plates incubated for 16–18 hours at 37° C. CTLL-2 proliferation in response to cytokines was measured by the MTT dye reduction assay. The reduction of the yellow MTT to a blue formazan is proportional to the number and metabolic rate of the CTLL-2 cells. To this end, 20 µl of a 5mg/ml sterile solution of MTT was added to all wells and the plates incubated for 6 hours at 37° C. The reduced MTT formazan was solubilized with acid isopropanol and the absorbance of each well was measured in an ELISA plate reader equipped with a 570 nm filter. The response was compared to a standard curve prepared by adding purified recombinant IL-2 to parallel cultures of CTLL-2 cells.

Influenza virus PR8-infected EL4 cells (multiplicity of infection of 10) and influenza virus nucleoprotein peptide NP366–374 served as positive controls. EL4 cells infected with the same *S. typhimurium* strains expressing the influenza virus nucleoprotein not fused to the SptP protein (NP) and therefore unable to be delivered into host cells served as negative controls. The results are shown in Table 2.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

TABLE 1

Bacterial strains used in this study.

| Strains | Relevant Genotype | Reference or source |
|---|---|---|
| *S. typhimurium* | | |
| SL1344 | rpsL hisG | (Hoiseth and Stocker 1981) |
| SB136 | rpsL hisG invA::aphT | (Galan et al. 1992) |
| SB225 | rpsL hisG sipA::aphT | (Kaniga et al. 1995) |

TABLE 1-continued

Bacterial strains used in this study.

| Strains | Relevant Genotype | Reference or source |
|---|---|---|
| SB169 | rpsL hisG sipB::aphT | (Kaniga et al. 1995) |
| SB220 | rpsL hisG sipC::aphT | (Kaniga et al. 1995) |
| SB221 | rpsL hisG sipD::aphT | (Kaniga et al. 1995) |
| SB237 | rpsL hisG sptP::aphT | (Kaniga et al. 1996) |
| χ3625 | rpsL hisG aroA::Tn10 | (Hoiseth and Stocker 1981) |

TABLE 2

Class I-restricted antigen presentation following challenge of antigen presenting cells with *S. typhimurium* expressing SptP-NP.

| Challenge | Hybridoma | IL-2 (pg) |
|---|---|---|
| PR8 | 12.164 | 800 ± 70 |
| PR8 | 7.9.3.28 | 4167 ± 320 |
| NP366–374 | 12.164 | 213 ± 10 |
| NP366–374 | 7.9.3.28 | 1250 ± 80 |
| SL1344 (SptP-NP) | 12.164 | 172 ± 10 |
| SL1344 (SptP-NP) | 7.9.3.28 | 300 ± 18 |
| SL1344 (NP) | 12.164 | <20* |
| SL1344 (NP) | 7.9.3.28 | <20* |
| χ3625 (SptP-NP) | 12.164 | 314 ± 30 |
| χ3625 (NP) | 12.164 | <20* |

*This values were considered negative as they were below the detection range of the assay

REFERENCES

Aggarwal, A., et al., *J Exp Med* 172:1083–1090 (1990).
Allen, P. M., *Immunol Today* 8:270–273 (1987).
Brett, S. J., et al., *J Immunol* 150:2869–2884 (1993).
Carter, P. and Collins, F., *J Exp Med* 139:1189–1203 (1974).
Cebra, J. J., et al., *Cold Spring Harbor Symp Quant Biol* 41:201–215 (1976).
Chain, B. M., et al., *Immunol Rev* 106:33–58 (1988).
Chen, L. M., et al., *Mol Microbiol* 21:1101–1115 (1996).
Chen, Y., et al., *EMBO J* 15:3853–3860 (1996).
Collazo, C. and Galan, J. E., *Infect Immun* 64:3524–3531 (1996).
Curtiss, R., et al., in Virulence Mechanisms of Bacterial Pathogenesis, R. Roth, Ed. (American Society for Microbiology, Washington, D.C., 1988) pp. 311–328.
Curtiss, R., et al., *Res Microbiol* 141:797–805 (1990).
Doggett, T. A. and Curtiss, R., *Adv Exp Med Biol* 327:165–173 (1992).
Flynn, J. L., et al., *Molec Microbiol* 4:2111–2118 (1990).
Galan, J. E., *Molecular Microbiol* 20:263–271 (1996).
Galan, J. E. and Bliska, J. B., *Ann Rev Cell Dev Biol* 12:219–253 (1996).
Galan, J. E., et al., in Proc V Internat Cong Equine Infect Dis, D. Powell, Ed. (University of Kentucky Press, 1988) pp. 34–40.
Galan, J. E., et al., *J Bacteriol* 17:4338–4349 (1992).
Galan, J. E., et al., *Infection & Immunity* 54:202–206 (1986).
Galan, J. E. and Timoney, J. F., *Infection & Immunity* 47:623–628 (1985).
Ganguly, R. and Waldman, R., *Prog Allergy* 27:1–68 (1980).
Gao, X. M., et al., *Infect Immun* 60:3780–3789 (1992).
Hakansson, S., et al., *Mol Microbiol* 20:593–603 (1996).
Harding, C. V., et al., *Immunol Rev* 106:77–92 (1988).
Hoiseth, S.K. and Stocker, B. A., *Nature* 291:238–239 (1981).

Kaniga, K., et al., *J Bacteriol* 177:7078–7085 (1995a).
Kaniga, K., et al., *J Bacteriol* 177:3965–3971 (1995b).
Kaniga, K., et al., *Mol Microbiol* 21:633–641 (1996).
Kaufman, S. H. E., *Immunol Today* 9:168–174 (1988).
Long. E. O. and Jacobson, S., *Immunol Today* 10:45–48 (1989).
Long, E. O., *Immunol Today* 10:232–234 (1989).
Persson, C., et al., *Molecular Microbiol* 18:135–150 (1995).
Rosqvist, R., et al., *EMBO J* 13:964–972 (1994).
Sambrook, et al., Molecular Cloning: A Laboratory Manual, 2d Edition, Cold Spring Harbor Laboratory Press, Cold Spring Harbor, New York (1989).
Sory, M.-P., et al., *Proc Natl Acad Sci USA* 92:11998–12002 (1995).
Sory, M.-P. and Cornelis, G. R., *Molec Microbiol* 14:583–594 (1994).
Takeuchi, A., *Am J Pathol* 50:109–136 (1967).
Tite, J. P., et al., *Immunology* 70:540–546 (1990a).
Tite, J. P., et al., *Immunology* 71:202–207 (1990b).
Yang, D. M., et al., *J Immunol* 145:2281–2285 (1990).

What is claimed is:

1. A method of stimulating a class I-restricted immune response to a protein of interest or immunogenic portion thereof in a mammalian host, said method comprising:
   introducing a nucleic acid molecule into a live avirulent *Salmonella typhimurium* having a type III secretion system, said nucleic acid molecule comprising a promoter operably linked to a segment encoding a chimeric protein, said chimeric protein comprising a protein of interest or immunogenic portion thereof and an injectable protein secretable by the type III secretion system or an injectable portion thereof; and introducing the resulting *Salmonella typhimurium* into a mammalian host, wherein the resulting *Salmonella typhimurium* injects the chimeric protein into the cytosol of cells of the mammalian host using the type III secretion system, thereby stimulating a class I-restricted immune response to the protein of interest or immunogenic portion thereof in the mammalian host.

2. The method of claim 1 wherein the protein of interest comprises an endogenous protein of a microbial pathogen.

3. The method of claim 1 wherein the injectable protein is an injectable protein of Salmonella.

4. The method of claim 1 wherein the injectable protein is an injectable protein of Yersinia.

5. The method of claim 1 wherein the injectable protein is an injectable protein of Shigella.

6. A protein delivery vehicle comprising:

a live avirulent *Salmonella typhimurium* having a type III secretion system, said *Salmonella typhimurium* comprising a nucleic acid molecule comprising a promoter operably linked to a segment encoding a chimeric protein, the chimeric protein comprising a protein of interest or an immunogenic portion thereof and an injectable protein secretable by the type III secretion system or an injectable portion thereof.

7. The protein delivery vehicle of claim 6 wherein the protein of interest comprises an endogenous protein of a microbial pathogen.

8. The protein delivery vehicle of claim 6 wherein the injectable protein is an injectable protein of Salmonella.

9. The protein delivery vehicle of claim 6 wherein the injectable protein is an injectable protein of Yersinia.

10. The protein delivery vehicle of claim 6 wherein the injectable protein is an injectable protein of Shigella.

11. A chimeric protein comprising:
- a first amino acid sequence of an injectable protein secretable by a type III secretion system or an injectable portion thereof; and
- a second amino acid sequence of a protein of interest or immunogenic portion thereof introduced into the first amino acid sequence of the injectable protein or injectable portion thereof.

12. The chimeric protein of claim 11 wherein the protein of interest comprises an endogenous protein of a microbial pathogen.

13. The chimeric protein of claim 11 wherein the injectable protein is an injectable protein of Salmonella.

14. The chimeric protein of claim 11 wherein the injectable protein is an injectable protein of Yersinia.

15. The chimeric protein of claim 11 wherein the injectable protein is an injectable protein of Shigella.

16. A chimeric nucleic acid molecule comprising:
- a first nucleic acid sequence encoding an injectable protein which is secretable by a type III secretion system or an injectable portion thereof; and
- a second nucleic acid sequence encoding a protein of interest or immunogenic portion thereof introduced into the first nucleic acid sequence of the injectable protein or injectable portion thereof, the second nucleic acid sequence being introduced so as to produce a chimeric nucleic acid molecule encoding a chimeric protein comprising the protein of interest or immunogenic portion thereof and the injectable protein or injectable portion thereof.

17. The chimeric nucleic acid molecule of claim 16 wherein the protein of interest comprises an endogenous protein of a microbial pathogen.

18. The chimeric nucleic acid molecule of claim 16 wherein the injectable protein is secretable by any type III secretion system of any bacteria.

19. The chimeric nucleic acid molecule of claim 16 wherein the injectable protein is an injectable protein of Yersinia.

20. The chimeric nucleic acid molecule of claim 16 wherein the injectable protein is an injectable protein of Shigella.

* * * * *